(12) United States Patent
Alam et al.

(10) Patent No.: US 7,217,242 B2
(45) Date of Patent: May 15, 2007

(54) ULTRASONIC METHOD FOR VISUALIZING BRACHYTHERAPHY SEEDS

(75) Inventors: Sheikh Kaisar Alam, Somerset, NJ (US); Ernest Joseph Feleppa, Rye, NY (US); Frederic Louis Lizzi, Tenafly, NJ (US)

(73) Assignee: Riverside Research Institute, New York, NY (US)

( * ) Notice: Subject to any disclaimer, the term of this patent is extended or adjusted under 35 U.S.C. 154(b) by 215 days.

(21) Appl. No.: 10/387,273

(22) Filed: Mar. 12, 2003

(65) Prior Publication Data

US 2004/0039284 A1   Feb. 26, 2004

Related U.S. Application Data

(60) Provisional application No. 60/363,452, filed on Mar. 12, 2002.

(51) Int. Cl.
*A61B 8/00* (2006.01)
*A61N 5/00* (2006.01)

(52) U.S. Cl. .......................... 600/439; 600/453; 600/3

(58) Field of Classification Search ................ 600/3–8, 600/439, 453–458
See application file for complete search history.

(56) References Cited

U.S. PATENT DOCUMENTS 5,178,147 A * 1/1993 Ophir et al. ................ 600/437
5,836,882 A * 11/1998 Frazin ........................ 600/462
6,129,670 A * 10/2000 Burdette et al. ............. 600/427
6,368,275 B1 * 4/2002 Sliwa et al. ................. 600/437
6,447,438 B1 * 9/2002 Bernardi et al. ............... 600/3
6,494,834 B2 * 12/2002 Konofagou et al. ......... 600/438
6,514,204 B2 * 2/2003 Alam et al. ................. 600/442
6,632,176 B2 * 10/2003 McIntire et al. ............ 600/439
6,689,043 B1 * 2/2004 McIntire et al. ............... 600/1
6,749,554 B1 * 6/2004 Snow et al. .................... 600/3

FOREIGN PATENT DOCUMENTS

WO   WO 03/015864   *   2/2003

OTHER PUBLICATIONS

Mcaleavey, S. WO 03015864 A2, Feb. 27, 2003.*

* cited by examiner

*Primary Examiner*—Francis J. Jaworski
(74) *Attorney, Agent, or Firm*—Baker Botts L.L.P.

(57) ABSTRACT

Methods are provided for enhancing the image of brachytherapy seeds implanted in tissue using a transrectal ultrasound apparatus. In a first arrangement the resonance of the seeds is determined and the seeds are insonified using acoustic signals having a resonance frequency of the seeds to cause the seeds to vibrate. The vibrating seeds have enhanced detection using a Doppler ultrasound device. In a second arrangement the acoustic signature of the seeds is determined and used to enhance the imaging of the seeds using a correlation function. In a third arrangement images are taken of the tissue and implanted seeds prior to and during the application of mechanical stress to the tissue. A correlation between the unstressed and stressed tissue can cause enhanced imaging of the seeds.

7 Claims, 3 Drawing Sheets

ULTRASONIC METHOD FOR VISUALIZING BRACHYTHERAPHY SEEDS

REFERENCE TO RELATED APPLICATIONS

This application claims the benefit of U.S. Application Ser. No. 60/363,452, filed Mar. 12, 2002.

BACKGROUND OF THE INVENTION

The present invention was made in connection with a grant from the National Institute of Health Grant R21 CA88231

Permanent interstitial implantation of iodine or palladium radioactive seeds is currently used for the treatment of prostate cancer. In connection with the implantation of such brachytherapy seeds a transrectal ultrasound (TRUS) examination of the prostate is used in the operating room. The TRUS probe is mounted on a fixture that contains a needle guidance template, which rests against the perineum and incorporates detents enabling the probe to be introduced into or withdrawn from the rectum in 5-mm steps. Scans are oriented in a transverse plane perpendicular to the probe axis. The fixture is advanced into the rectum until the seminal vesicles are imaged and scans are performed in planes separated by 5 mm as the probe is withdrawn. During the scans, the prostate is constrained against movement by position-fixing needles.

TRUS images are ported through a standard output jack to a laptop computer on which treatment-planning software is run. Such software may, for example, be VariSeed provided by Varian Medical Systems, Inc. (VMSI), Charlottesville, Va. This treatment planning software generates an image of available and optimal needle locations, which are fixed by the template used for needle guidance. The oncologist demarcates the prostate in each scan plane and prescribes a radiation dose for the glad as a whole. The planning software then presents a set of suggested seed positions in each scan plane, which the oncologist can accept or reject based on isodose distributions plotted by the software for whatever seed positions are chosen.

The software bases the isodose distributions on seed locations in the 3-D volume spanned by the set of scan planes in the planning set. Immediately after planning is completed, seed-implantation needles are loaded with the radioactive seeds and plastic spacer seeds in a manner that places radioactivity at the specified depths, corresponding to the scan planes, along each needle position. The spacers are not visible in ultrasonic or x-ray computed tomography (CT) images. Loaded needles are then inserted into the prostate via the perineum through the template holes that match the needle positions depicted on the planning-software image. Dosimetric evaluation subsequently is performed using post-implant CT imaging. Traditionally, post-implant CT scans are performed within two weeks of implantation, but in some cases they are performed within 24 hours of implantation.

In some cases, the CT scans show that the actual location of implanted seeds differs from their planned locations. Studies by Potters, et al., have shown that 30% of prostate brachytherapy procedures result in a dose to 90% of the prostate that is less than the prescribed dose. [Potters, et al., Int. J. Radiat. Oncol. Biol. Phys., 50:605–614, 2001] Studies by Stock, et al., showed that 32% of under-dosed patients have biochemical failure (as evidenced by a rise in the blood level of prostate-specific antigen (PSA)) within four years, where as only 8% of properly dosed patients have biochemical failure. [Stock, et al, Int. J. Radiat. Oncol. Biol. Phys., 41:101–108, 1998] The conventional B-mode ultrasound images generated at the time of the procedure do not allow adequate visualization of the placed seeds because of clutter, shadowing and the loss of echo signals due to seed angulation. Clutter often increases immediately during the procedure from hemorrhage and edema caused by the trauma of needle insertion.

It is an object of the present invention to provide improved imaging of implanted seeds during the implantation process with the result that seed implantation errors can be corrected, for example by implantation of additional seeds during the procedure.

SUMMARY OF THE INVENTION

In accordance with a first embodiment of the invention there is provided a method for ultrasonically imaging implanted therapeutic seeds in tissue. The method includes determining acoustic reflection properties of the seeds in response to acoustic signals from an ultrasonic probe having selected signal characteristics. The selected signal characteristics may include a scanned beam to create two-dimensional images of the tissue and embedded seeds. The tissue and the seeds are insonated using acoustic signals having the selected signal characteristics and reflected acoustic signals are received from the tissue and the seeds. The reflected acoustic signals are analyzed using a correlation algorithm to generate an image of the tissue and the seeds with image portions corresponding to the seeds enhanced by the correlation algorithm.

In a preferred arrangement of the first embodiment, acoustic reflection properties are determined by isolating at least one of the seeds in an acoustically transparent medium and acquiring reference reflected radio-frequency (RF) echo signals from the seeds in response to acoustic signals from the same ultrasonic probe at same settings. The analyzing may be done by performing a two-dimensional correlation analysis of two-dimensional RF echo signals of scans of embedded seeds in the prostate with the two-dimensional reference RF echo signals. The analysis may use a normalized or an unnormalized correlation function.

In accordance with a second embodiment of the invention there is provided a method for ultrasonically imaging implanted brachytherapy seeds in tissue. First, the tissue is insonated in a two dimensional scanning mode using acoustic signals from an ultrasonic probe having selected signal characteristics and reflected acoustic signals are received from the tissue and the seeds. Second, the tissue containing the seeds then is mechanically deformed and the tissue and the seeds are insonated again using the same acoustic signals having the selected signal characteristics following the mechanical deformation, and reflected acoustic signals again are received from the tissue and the seeds. Correlation analysis is applied on the first and second reflected acoustic signals on a window-by-window basis and, a display of a correlation map of the first and second reflected signals is generated and displayed. The seeds typically exhibit a higher correlation value than the tissue, especially if the deformation is large.

In a preferred arrangement of the practice of the second embodiment reflected signals are received by acquiring RF signals for the first and second reflected acoustic signals after high strains are applied that are sufficient to decorrelate signals from tissue that is not mechanically stiff compared to rigid metallic seeds while retaining the correlation of signals from mechanically much stiffer seeds. Either a one-dimensional or a two-dimensional correlation analysis (using either unnormalized or normalized correlation function) of the acquired RF signals (or its envelope) may be performed.

In accordance with a third embodiment of the invention there is provided a method for ultrasonically imaging implanted therapeutic seeds in tissue. The method includes determnining at least one mechanical resonance frequency for the seeds. The implanted seeds are stimulated with a first acoustic signal having a frequency corresponding to its resonance frequency to cause the seeds to vibrate at the resonance frequency. The tissue and the seeds are imaged using second acoustic signals and a Doppler method is used to sense the vibratory motion of the seeds. The second acoustic signals have a frequency higher than the resonance frequency.

In accordance with a preferred practice of the third embodiment the mechanical resonance frequency is determined by embedding a sample seed of the seed type of interest in an appropriate medium that is mechanically equivalent to a prostate gland, and placing the embedded seed in the overlapping fields of two transducers. A first transducer is driven with signals having various frequencies and the response of the second transducer is observed to determine signal peaks indicating resonance.

The stimulating may comprise insonating the tissue along a first axis and the imaging may comprise insonating the tissue along a second axis, which may be different from or the same as the first axis. Alternately, an array can be arranged with a central, high-frequency linear-array or mechanical-scanning portion which images the seed—or the gland that contains the seed—and two larger, unfocussed elements on either side or an element that surrounds the scanning array that provides the resonance-stimulating ultrasound. In this case, the two axes would be the same.

For a better understanding of the present invention, together with other and further objects, reference is made to the following description, taken in conjunction with the accompanying drawings, and its scope will be pointed out in the appended claims.

DESCRIPTION OF THE PREFERRED EMBODIMENTS OF THE INVENTION

Figure 1:
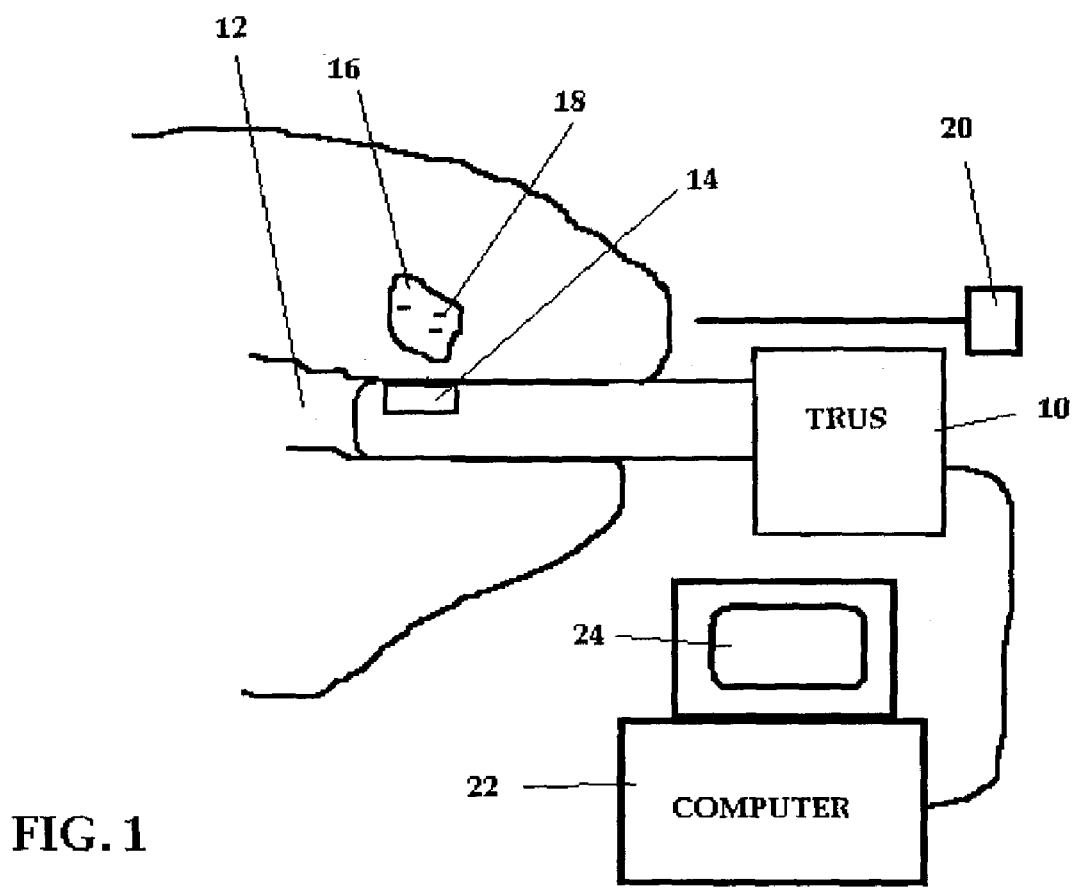
FIG. 1 is a drawing illustrating an arrangement that can be used to practice a first embodiment of the invention.

A first embodiment of the method of the present invention will be described with reference to FIGS. 1 through 3. As used herein, the term therapeutic seeds includes brachytherapy seeds, which are well known, and other seeds of similar dimension which may be used for delivering a therapeutic agent to a localized region. Shown in FIG. 2 is a typical palladium seed 18 currently used in connection with brachytherapy of the prostate. The seed includes a thin cylindrical shell 26 of titanium, having overall dimensions of 4.5-mm length and 0.8-mm diameter. Different types of radioactive palladium and iodine seeds have different amounts of interior space and solid material. The illustrative palladium seed has graphite plugs 30, 32 at each end of the interior space 28, that is coated with radioactive palladium. The seed also contains a central lead plug 34, which is provided to enhance visibility on post-implantation CT scans. Iodine seeds come in a wide variety of configurations, but all seeds have the same external cylindrical dimensions. Ultrasonic reflections from the seed 18 are specular, and tilting the seed axis away from perpendicular to the beam markedly reduces the amount of reflected energy returned to the transducer. The curvature of the seed causes it to be imaged as a fine-wire profile of the incident beam. The seed has indented cup ends, as shown in FIG. 2, which typically trap air, which may confound the ultrasonic properties of the seeds.

Figure 3:
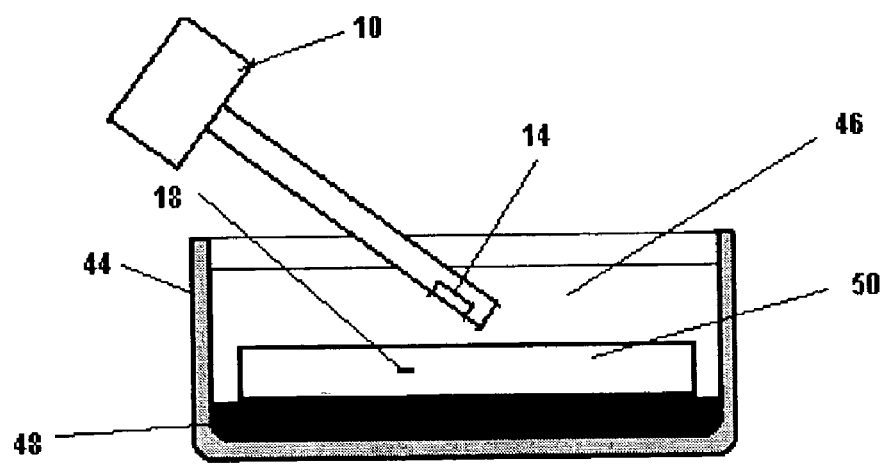
FIG. 3 is a drawing illustrating the acquisition of reflective characteristic data for a brachytherapy seed in connection with practice of the embodiment of FIG. 1.

Referring to FIG. 3, there is shown an arrangement for obtaining an ultrasound echo "signature" of a brachytherapy seed 18. A transrectal ultrasonic probe 10, having a radiation aperture 14 is immersed in water 46 contained in a vessel 44. A brachytherapy seed 18, or a non-radioactive replica thereof, is placed within an acoustically transparent medium 50 immersed in water 46. An absorbent medium 48 supports transparent medium 50. RF echoes from seed 18 are digitally acquired in two dimensions by scanning the beam in the acoustically transparent medium using the same signal characteristics, such as settings of power, time-gain control, fixed gain, and so forth, that are used for brachytherapy procedures. This procedure acquires an acoustic signature for the brachytherapy seed 18 for use in subsequent procedures.

Figure 2:
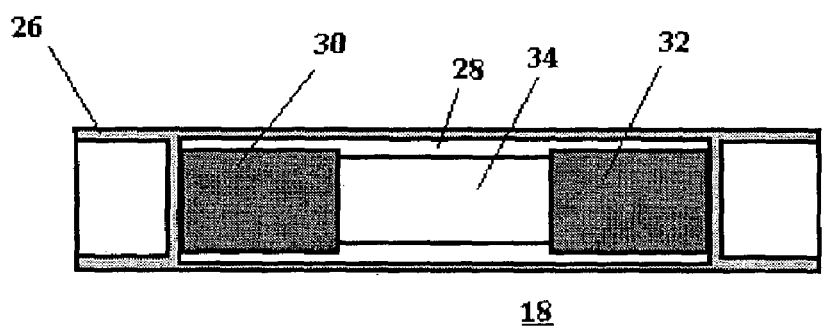
FIG. 2 is a cross-sectional view of a typical brachytherapy implant seed containing radioactive palladium.

Referring to FIG. 1 there is shown an arrangement useful for practice of a first embodiment of the method of the present invention. A transrectal probe 10 having an aperature 14 is inserted in the rectal canal 12 of a patient in an arrangement to insonate prostate 16 in which brachytherapy seeds 18 have been placed using an insertion device 20. RF data from the transrectal ultrasound device 10 is acquired by a computer 22 having a display 24. During a seed implantation procedure digital RF echo signal data from transrectal ultrasound probe 10 are acquired in two dimensions by the computer by scanning the beam used to image the seed bearing prostate 16. Computer 22 performs a two-dimensional correlation analyses between reference signature signals from an isolated seed and the signals from the entire prostate scan plane and thereafter displays correlation maps on display 24. Correlations can be performed using RF or envelope-detected signals, and the results can be computed as either normalized or unnormalized correlation coefficients. Depending on the processing option, the displayed correlation maps show either localized bright spots or a distinctive pattern at the apparent location of implanted seeds.

A suitable normalized correlation function is as follows:

$$\rho_{xy}[i][j] = \frac{\sum_{m=0}^{M-1}\sum_{n=0}^{N-1}\{x[m,n]-\bar{x}\}\{y[m+i,n+j]-\bar{y}\}}{\sqrt{\sum_{m=0}^{M-1}\sum_{n=0}^{N-1}\{x[m,n]-\bar{x}\}^2\sum_{k=0}^{M-1}\sum_{l=0}^{N-1}\{y[k+i,l+j]-\bar{y}\}^2}}$$

A suitable unnormalized correlation function is as follows:

$$C_{xy}[i][j] = \sum_{m=0}^{M-1}\sum_{n=0}^{N-1} \{x[m,n] - \bar{x}\}\{y[m+i, n+j] - \bar{y}\}.$$

In connection with obtaining good correlation results using RF data it was found to be helpful to provide jitter correction. In connection with using unnormalized correlation values, a depth dependent compensation was applied to the data using an empirical value of 0.5 dB per MHz-cm for the attenuation coefficient. Unnormalized correlation analysis using envelope detected RF signals also depicted the seeds as bright areas which was similar to results from RF correlation analyses. Normalized correlation analyses using the echo signal envelope produces sharp bright spots surrounded by distinctive pattern where implanted seeds are present.

Figure 4:
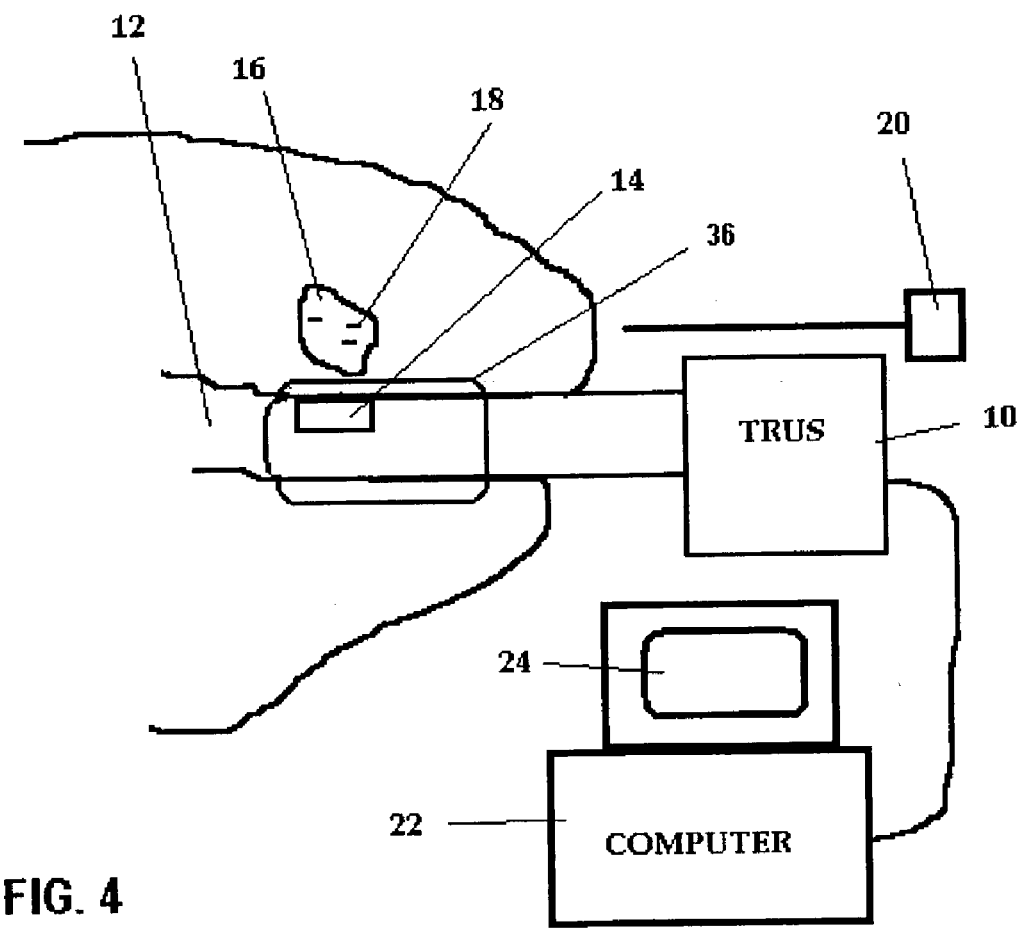
FIG. 4 illustrates the practice of a second embodiment of the invention.

Referring to FIG. 4 there is shown a second embodiment of the method of the present invention. In connection with the second embodiment a transrectal probe 10 is likewise used for providing a display of the prostate 16 and implanted seeds 18 during an implantation procedure. In the method illustrated in FIG. 4 a reference measurement is made using transrectal ultrasound probe 10 to obtain data representing acoustic reflections from prostate 16 and implanted seed 18. Thereafter mechanical stress is applied to the tissue, compressing prostate 16 and the measurement of echo signals is repeated. One method for applying mechanical stress is to displace the probe toward the prostate. Another technique, illustrated in FIG. 4, is to fill a balloon 36 surrounding probe 10 with fluid to compress the surrounding tissue. In a preferred embodiment, three or more measurements may be made of the acoustic reflections from prostate 16 and implanted seeds 18 using varying amounts of applied mechanical stress.

The second embodiment is based on cross-correlation analyses of echo signals from tissue before and after a high-strain deformation. In typical implementations of elastography applied to tissue, compression and deformation must be small in order to prevent decorrelation. In contrast, because the brachytherapy seeds are extremely stiff compared to tissue, they do not measurably distort upon compression, and large deformations beneficially decorrelate tissue signals, while retaining the correlation in signals from undeformed implanted seeds. At excessive strains, seeds may undergo complex motion, including out of plane motion and rotation, which can reduce correlation. The transducer axis is approximately perpendicular to the long axis of the seed. At least one RF frame is acquired before compression and one or more RF frames are acquired after each compression step. A one or two-dimensional correlation analysis between pre and post-deformation RF echo signals or their envelope signals may be applied to quantify seed displacement and to evaluate echo signal shape changes during displacement. The resultant correlation maps can then be displayed with an envelope detected scan image for comparison. The soft tissue surrounding the seed implant will decorrelate thus displaying the seeds as regions with a high correlation coefficient value.

Figure 5:
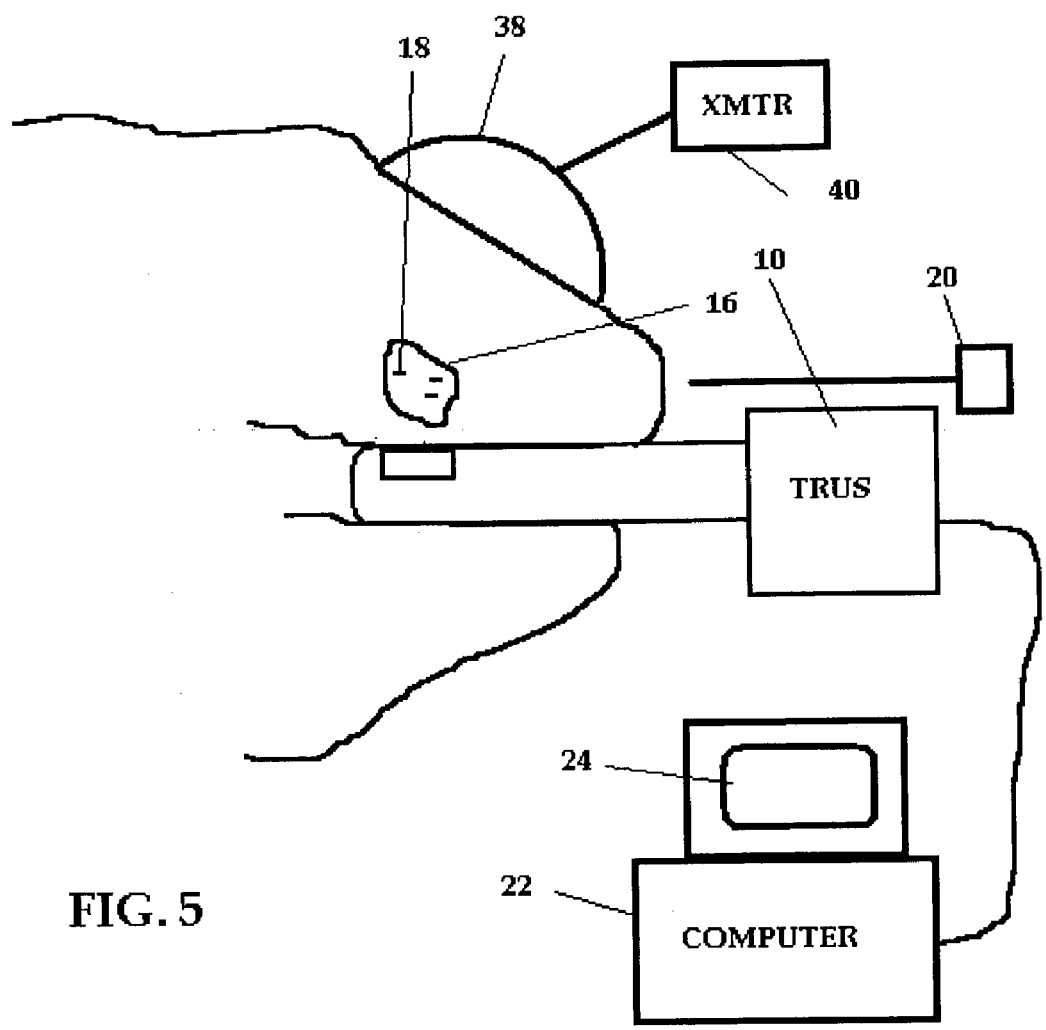
FIG. 5 illustrates the practice of a third embodiment of the invention.
Figure 6:
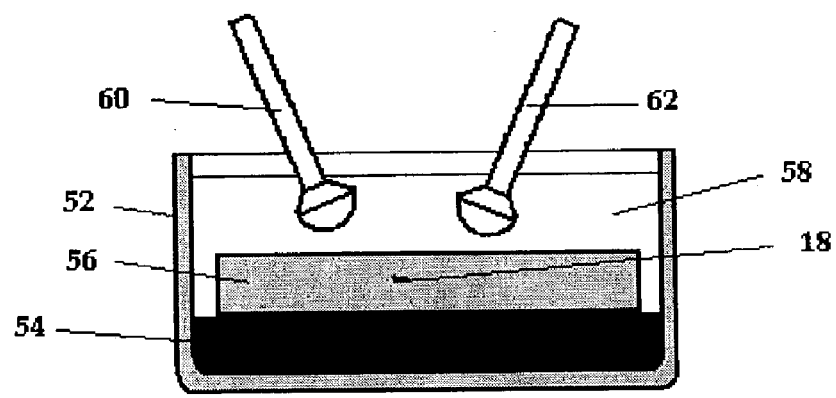
FIG. 6 illustrates a method for determining resonance frequency of brachytherapy seeds in connection with practice of the third embodiment of the invention.

Referring to FIGS. 5 and 6 there is shown a third embodiment of the method of the present invention. The third embodiment is based on determining the resonance characteristics of the implanted seeds with respect to acoustic signals. The resonance vibration of excited seeds can be detected and imaged using Doppler ultrasound.

Referring to FIG. 6 there is shown an experimental determination of the natural resonance frequencies of palladium seeds with a resonance ultrasound spectroscopy apparatus. In this apparatus a small seed-simulating sample 18 is embedded in suitable material 58 having mechanical properties equivalent to prostate tissue and placed in the overlapping fields of a lower frequency resonance stimulating piezo electric transducers 60 and a higher frequency imaging transducer 62. By sweeping frequency of signals applied to the resonance stimulating transducer and detecting the frequencies at which Doppler components reach maxima in the signal received by the higher frequency transducer, it is possible to determine mechanical resonance frequencies of the sample 18.

In the apparatus indicated in FIG. 6, sample 18 was placed within a section 56 of simulated tissue, such as animal liver tissue and mounted on an ultrasound absorbing rubber block 54 placed at the bottom of a vessel 52. Water 58 is placed in the vessel sufficient to cover the radiating portions of transducers 60 and 62. When simulated seed 18 is excited with ultrasound signals at a resonance frequency, strong Doppler signals were detected through the receiving transducer. Standard simulated seeds have shown a resonance at about 1 MHz. This frequency is far below the range of conventional diagnostic ultrasound scanners used for prostate imaging. The resonant frequency of the seeds can also be determined with a Resonant Ultrasound Spectroscopy apparatus.

FIG. 5 illustrates a procedure for imaging a prostate 16 and implanted seeds 18 in a patient. Images are acquired by transrectal ultrasound unit 10 and supplied to computer 22 having display 24, after seeds 18 have been implanted in prostate 16 using insertion device 20. During the imaging process a transmitter 40 provides a signal to low frequency transducer 38, such as an airbacked therapeutic transducer, which insonifies prostate 16 with acoustic signals at a resonance frequency of seeds 18. The signals from transducer 38 cause seeds 18 to mechanically resonate, which should be easily detected using color/power Doppler detection of the output of transrectal ultrasound device 10. It is believed that the insonification angle of the low frequency resonant acoustic signals provided to prostate 16 should be at an angle, for example 45 degrees, away from the resonance-stimulating transducer axis. It has been experimentally determined that a relatively low intensity of the ultrasound provided by transducer 38, for example an intensity of about 13.5 mW per square cm., provides adequate resonant excitation of seeds 18 to enable a Doppler detection to occur which effectively enhances the imaging of the seeds on display 24.

While there have been described what are believed to be the preferred embodiments of the invention, those skilled in the art will recognize that other and further changes and modifications may be made thereto without departing from the spirit of the invention, and is intended to claim all such changes and modifications as fall within the true scope of the invention.

We claim:

1. A method for ultrasonically imaging implanted therapeutic seeds in tissue, comprising:
   determining at least one mechanical resonant frequency for said seeds;
   stimulating said seeds with first acoustic signals having a frequency corresponding to said resonant frequency to cause said seeds to vibrate at said resonant frequency; and imaging said tissue and said seeds using second acoustic signals and a Doppler method to sense vibratory motion, said second acoustic signals having a frequency higher than said resonant frequency.

2. A method as specified in claim 1 wherein said determining at least one mechanical resonant frequency comprises placing a sample of said seeds in the fields of two transducers, driving a first transducer with signals having variable frequency and observing the response of said second transducer to determine signal peaks indicating resonance.

3. A method as specified in claim 1 wherein said stimulating comprises insonating said tissue along a first axis and wherein said imaging comprises insonating said tissue along a second axis.

4. A method as specified in claim 3 wherein said first axis is the same as said second axis.

5. A method as specified in claim 3 wherein said second axis is different from said first axis.

6. A method for ultrasonically imaging implanted brachytherapy seeds in tissue, comprising:
   determining expected response properties of said seeds in response to an induced stimulus having selected signal characteristics;
   applying said stimulus to said tissue and said seeds and receiving reflected response signals from said tissue and said seeds; and
   analyzing said reflected response signals to generate an image of said tissue and said seeds; wherein said induced stimulus comprises an applied acoustic signal operating at a mechanical resonant frequency of said seeds and wherein said response signals comprise a resonant vibration of said seeds.

7. A method for ultrasonically imaging implanted brachytherapy seeds in tissue, comprising:
   determining expected response properties of said seeds in response to an induced stimulus having selected signal characteristics;
   applying said stimulus to said tissue and said seeds and receiving reflected response signals from said tissue and said seeds; and
   analyzing said reflected response signals to generate an image of said tissue and said seeds; wherein after said step of applying a stimulus, the method further comprises:
   ultrasonically insonating said tissue and said seeds using a first ultrasonic pulse and receiving first reflected ultrasonic echo signals from said tissue and said seeds;
   applying mechanical stress to said tissue;
   ultrasonically insonating said tissue and said seeds using a second ultrasonic pulse and receiving second reflected ultrasonic echo signals from said tissue and said seeds; and
   wherein said step of analyzing said reflected response signals comprises analyzing said first and second reflected ultrasonic echo signals and generating a display of a correlation map of the first and second reflected ultrasonic echo signals, thereby detecting the rigid body motion of said seeds, said seeds exhibiting higher correlation value than said tissue and displaying said seeds as higher correlation areas of appropriate size.

* * * * *